ID#

United States Patent [19]
Bahrmann et al.

[11] Patent Number: 5,174,899
[45] Date of Patent: Dec. 29, 1992

[54] PROCESS FOR SEPARATING ORGANOMETALLIC COMPOUNDS AND/OR METAL CARBONYLS FROM THEIR SOLUTIONS IN ORGANIC MEDIA

[75] Inventors: Helmut Bahrmann, Hamminkeln-Brunen; Michael Haubs, Bad Kreuznach; Willi Kreuder, Mainz; Thomas Muller, Dinslaken, all of Fed. Rep. of Germany

[73] Assignee: Hoechst Aktiengesellschaft, Fed. Rep. of Germany

[21] Appl. No.: 724,463

[22] Filed: Jun. 26, 1991

Related U.S. Application Data

[63] Continuation of Ser. No. 452,517, Dec. 18, 1989, abandoned.

[30] Foreign Application Priority Data

Dec. 20, 1988 [DE] Fed. Rep. of Germany ....... 3842819

[51] Int. Cl.⁵ .............................................. B10D 61/14
[52] U.S. Cl. ..................................... 210/644; 210/651
[58] Field of Search ............... 210/638, 651, 644, 652, 210/654, 500.23; 502/150

[56] References Cited

U.S. PATENT DOCUMENTS

| 3,853,754 | 12/1974 | Gosser | 502/150 X |
| 3,957,504 | 5/1976 | Ho et al. | 210/638 X |
| 3,966,595 | 6/1976 | Gosser | 210/651 X |
| 4,544,484 | 10/1985 | Sundet | 210/500.23 |

FOREIGN PATENT DOCUMENTS

| 325962 | 8/1989 | European Pat. Off. . |
| 2336763 | 1/1974 | Fed. Rep. of Germany . |
| 1266180 | 3/1972 | United Kingdom . |

*Primary Examiner*—Frank Spear
*Attorney, Agent, or Firm*—Jordan B. Bierman

[57] ABSTRACT

Organometallic compounds and/or metal carbonyls are separated from their solutions in organic media with the aid of semi-permeable membranes made of aromatic polyamides.

49 Claims, No Drawings

PROCESS FOR SEPARATING ORGANOMETALLIC COMPOUNDS AND/OR METAL CARBONYLS FROM THEIR SOLUTIONS IN ORGANIC MEDIA

This application is a continuation of application No. 07/452517, filed Dec. 18, 1989, now abandoned.

This application claims the priority of German P 38 42 819.9, filed Dec. 20, 1988.

The invention relates to a process for separation by membrane filtration of organometallic compounds and/or metal carbonyls dissolved in organic media, both classes of compounds being hereinafter referred to as metal compounds.

BACKGROUND OF THE INVENTION

Organic compounds and carbonyl compounds of the transition metals, in particular compounds containing a metal of the platinum group as the central atom, are being increasingly used as catalysts in industrial chemical processes. The recovery of the catalyst has a considerable influence on the economy of these processes. It should be recovered as completely and as simply as possible.

Therefore, there have been many attempts to develop techniques which satisfy these requirements. Two main routes have been pursued. The first restricts itself to recovering the catalyst metal and accepts the degradation of the catalytically active compound. Thermal cleavage, reduction, oxidation and precipitation steps dominate these processes. The aim of the other route is not to allow the catalytically active metal compound to be destroyed, but to recover it undamaged so that it can be recycled without any further treatment. The following deals in greater detail with this second variant for the recovery of organometallic compounds or metal carbonyls.

One possible route for separating organometallic coordination complexes from organic liquids consists in the use of selective separating membranes. Thus, DE-OS 19 12 380 describes a process in which a mixture of the complex with one or more organic components is brought into contact under pressure with one side of a cellulose membrane. The ratios of the molecular size and shape of the complex to molecular size and shape of the organic components are such that the material diffusing through the membrane has a reduced complex content.

DE-OS 19 53 641 describes a process for separating organometallic compounds from a solution of the compounds in an organic solvent by means of a membrane. This procedure is characterized in that a silicone rubber membrane is used. Furthermore, according to a process described in GB-PS 12 66 180, organometallic compounds are removed from their solutions in organic solvents by means of a polyamide membrane. Finally, DE-OS 24 14 306 describes the separation of organometallic compounds from organic solutions with a polyacrylonitrile membrane.

However, the aforementioned separating processes have the disadvantage that the membranes are not stable in the organic solvents, some of which attack the membranes; in particular, they swell when subjected to pressure and temperature loading and thus lose their beneficial properties. For this reason, no membrane process for such separations has been able to establish itself in industrial practice.

Therefore, the problem was to develop a process which permits the separation of organometallic compounds and/or metal carbonyls from organic media using membranes which not only exhibit the required separating properties under the selected operating conditions, but also are highly stable and thus permit simple and effective separation of the organometallic compounds or the metal carbonyls from organic media.

BRIEF DESCRIPTION OF THE INVENTION

The invention comprises a process for separating organometallic compounds and/or metal carbonyls from their solutions in organic media. It is characterized in that the solutions are brought into contact with a semipermeable membrane made of an aromatic polyamide (polyaramide). The force behind the separating process can be either a difference in pressure (pressure filtration) or a difference in concentration (dialysis).

Surprisingly, with the new process it is possible to recover organometallic compounds and/or metal carbonyls more or less completely and in unchanged form; i.e. without decomposition or change in any other way. In this context, it is particularly significant that the membrane does not lose its beneficial separating properties either through pressure, temperature, or other influences in the organic media.

DETAILED DESCRIPTION OF THE INVENTION

In the sense of the present invention, organometallic compounds are understood to be compounds in which carbon atoms of organic groups are bound to metal atoms. The metals include the so-called semimetals such as boron and silicon, as well as phosphorus. According to the invention organometallic compounds are also compounds soluble in an organic solvent in which the bond between the metal and carbon is formed by nitrogen, oxygen or sulfur. Examples of these compounds are acetyl acetonates and dimethylglyoximes.

The organometallic compounds, which also contain nitrogen and oxygen in addition to carbon, are preferably derived from the elements of the groups IVA, VA, VIA, VIIA, VIIIA and IB of the Periodic Table of the Elements. (All references to the Periodic Table herein are to the IUPAC Version). Organometallic compounds of manganese, cobalt, nickel, palladium, platinum, iridium, and rhodium have special importance.

The term metal carbonyls is not restricted to compounds consisting solely of metal and CO but also covers the compounds which also contain other ligands such as hydrogen, olefins, phosphanes, acetate, and benzonitrile. Suitable carbonyls are those of the metals of the groups VIA, VIIA and VIIIA of the Periodic Table; in particular, carbonyls of iron, cobalt, nickel, ruthenium, rhodium, and iridium.

The membranes used in accordance with the invention consist of an aromatic polyamide, also called polyaramide, and are already known. The polymers are obtained by polycondensation from aromatic dicarboxylic acids or dicarboxylic acid derivatives and aromatic diamines in a dipolar aprotic solvent. Suitable carboxylic acid components are, for example, terephthalic acid, 4,4'-diphenyldicarboxylic acid, 4,4'-diphenyletherdicarboxylic acid, 4,4'-diphenyl sulfone dicarboxylic acid, and 2,6-naphthalene dicarboxylic acid.

Suitable diamine components are p-phenylene diamine, 3,3'-dimethoxybenzidine, 3,3'dichlorobenzidine, 3,3'-dimethylbenzidine, 4,4'-diaminodiphenylmethane, 2,2-bis(4-aminophenyl)propane, and 1,4-bis(4-aminophenoxy)benzene.

Membranes of polyaramides containing various diamines as monomers in addition to a carboxylic acid component have gained special significance. Thus, for example, polyaramides synthesized from terephthalic acid with p-phenylene diamine, 1,4-bis(4-aminophenoxy)benzene, and/or 3,3'-dimethylbenzidine have proved successful. The amines can be statistically distributed in the polymers. The polyamides can, however, have the structure of block copolymers.

The average molecular weight of the polyaramides can range widely. Normally the range is 5,000 to 200,000. Polyaramides with a molecular mass of 10,000 to 50,000 are preferred.

A process which is described in German Patent Application P 38 02 030 has proved successful for manufacturing the claimed membranes. The membranes disclosed in this publication consist of a copolyamide which is synthesized from three different diamines and a dicarboxylic acid. A solution of this copolyamide in an aprotic polar solvent of the amide type, e.g. N-methyl-2-pyrollidone, is spread onto a flat surface as a liquid layer. The precipitating liquid, in particular water, which is miscible in the solvent of the solution, is added to the liquid layer and precipitates the polymer as a membrane. The precipitating liquid is left to act on the precipitated membrane until the solvent has been completely replaced by the precipitating liquid. If necessary, the membrane can be subjected to heat treatment. Then the membrane is dried, optionally after prior treatment with glycerin.

The membranes prepared according to the process described above are integrally asymmetric and are known in principle to one skilled in the art. The membranes have a very thin, active separating layer whose thickness is 0.05 to 5$\mu$ and a porous supporting structure. The thickness of the membrane consisting of active separating layer and supporting structure can be 10 to 400$\mu$, it is preferably 50 to 200$\mu$.

The shape of the membrane can be selected at will. It can be a disc and, in particular, a hollow fiber or capillary, but can also have any shape suitable for the prescribed use. The decisive factor is to achieve maximum possible stability as possible and, moreover, as large a surface as possible per volume unit in order to attain a satisfactory throughput.

It is recommended to pretreat the membrane before use. In the simplest case it is immersed in the solution to be separated. However, other conditioning processes are also possible. If, for example, the membrane was prepared by precipitation with water, the water is replaced, e.g. by i-propanol by placing the membrane in i-propanol and replacing the alcohol several times. Then the i-propanol is replaced in the same manner by the organic medium in which the metal compounds to be separated are dissolved. The type and method of conditioning the membrane determine the operating conditions to be observed in the claimed process. With a given dissolved metal compound, the decisive variables which can influence the separating process are the pressure applied, the temperature of the solution, the type of solvent and the concentration of the metal compound in the solution.

The separating procedure according to the claimed process can either be performed as pressure filtration or as dialysis. In the first case, a pressure must be maintained between the retentate and the permeate sides of the membrane which is greater than the osmotic pressure of the system, i.e. of the solutions of different concentration on both sides of the membrane. It is expedient if the difference in pressure across the membrane is 0.1 to 15 MPa, preferably 0.1 to 10 MPa and in particular 0.2 to 2 MPa (1 MPa being approximately 145 psi). In the second case a flushing solution is passed in countercurrent on the permeate side of the membrane. This process (called dialysis) is particularly advantageous in a hollow fiber or capillary module. Suitable flushing solutions are, for example, organic solvents. The operating temperatures of both process variants are 0° to 200° C. and in particular 40° to 130° C.

The concentrations in the feed solution of the metal compounds to be separated can vary widely. The claimed process makes it possible to successfully separate dissolved metal compounds whose concentration is only a few ppm as well as metal compounds whose concentration is measured in per cent. However, it has proved expedient if the concentrations of the organometallic compounds and/or the metal carbonyls in the organic medium do not exceed 20% by weight. With commercial processes, feed solutions containing 2 to 400 wt. ppm of the metal compounds are of significance and are used with particular success.

The linear flow velocity across the membrane ranges from 0.1 to 10 m/sec, preferably 0.5 to 2.5 m/sec.

The separating effect is probably due to the fact that the small components of the solutions used which, depending on its origin, contains, for example, unreacted starting materials, reaction products and, in some cases, a solvent or solvent mixture as a reaction medium, can diffuse through the active separating layer more easily than the metal compound. Thus, the greater the volume of the metal compound and the greater the difference in size between the metal compound and the other components of the solution, the better the separation. It is expedient if the metal compound has at least a 50% larger cross-section than the largest organic component. To get a rough approximation, the molecular weight of the components can be considered instead of the size of the molecule to assess the quality of the separation. It is advantageous if the difference in molecular weight between the metal compound and the organic components of the mixture is as great as possible.

The claimed process can be performed batchwise or continuously, in one or more stages. In general, the membrane is located outside the reaction zone so that reaction conditions and separating conditions, e.g. pressure and temperature, can be optimized independently of each other.

With the one-step variant, the feed solution is added to the membrane under pressure. In the simplest case the permeate is drawn off and the concentrated solution is removed from the separating device as soon as the desired concentration has been reached. This procedure can also be performed continuously to increase the separating efficiency. The feed solution then flows along the membrane, is concentrated and continuously drawn off, as is the permeate.

Multi-stage separation is performed with separating stages either in parallel or in series. The series configuration, in which the permeate is separated in every stage and the concentrated solution is passed to the next separating stage, permits particularly effective use of the available system pressure, i.e. the operating pressure in the previous process step, and permits the recovery of more highly concentrated solutions. If, on the other hand, the permeate is passed into consecutive separating stages, the dissolved substances can be more or less completely recovered regardless of the number of separating stages.

When using the process variants described above, the separating efficiency of the membrane can be further improved by increasing the flow rate over the membrane by means of a circulating pump.

Finally, by flowing a flushing solution on the permeate side of the membrane concurrently and preferably countercurrently to the flow on the feed side, the concentration of the dissolved substance in the permeate can be reduced and thus the driving force (difference in concentrations) increased (dialysis principle).

The new process has, inter alia, proved to be admirable for separating organometallic compounds and/or metal carbonyls from reaction solutions in which they have, for example, been used as homogeneous catalysts. The following metal complex compounds soluble in organic media and the reactions which are catalyzed by them are given merely as examples of such compounds: Ni/Al complex compounds, e.g. i-$C_4H_9AlCl_2$. /$NiCl_2[P(C_6H_5)_3]$ for the dimerization of butadiene to trans-1,4-hexadiene and of butene to octenes; Co/Al complex compounds, e.g. i-$C_4H_9AlCl_2$. /$CoCl_2[P(C_6H_5)_3]_2$ for dimerization of butadiene to cis-1,4-hexadiene; phosphite-modified Ni/Al-alkyl compounds for the preparation of cyclooctadiene from butadiene; $Pd(CH_3COO)_2/P(C_2H_5)_3$ complex compounds for the preparation of octadiene-1,7; $RuHCl[P(C_6H_5)_3]_3$ or $RhCl[P(C_6H_5)_3]_3$ for the homogeneous hydrogenation of olefins; $RhCO[P(C_6H_5)_3]_2$ for the hydroformylation of formaldehyde; $Ni[P(p-C_6H_4 CH_3)_3]_4/H$ for the hydrocyanation of butadiene; $Ir(COD)[P(C_6H_{11})_3]Py$ (COD = 1,5-cyclooctadiene, Py = pyridine) for the hydrogenation of cyclic alkenes; $RuCl_2[P(C_6H_5)_3]$ for the hydrogenation of terminal alkenes; [Ru(BINAP)] $(ClO_4)_2$ (BINAP = 2,2'bis(diphenylphosphino)1,1'-binaphthyl) for the asymmetric hydrogenation of olefinic double bonds; $HRhCO[P(C_6H_5)_3]_3$ for the hydroformylation of alpha-olefinic compounds such as allyl alcohol; $Pd[P(C_6H_5)_3]_4$ for the nucleophilic alkylation of allyl systems and the functionalizing oligomerization of butadiene; rhodium complex compounds such as $HRhCO[P(C_6H_5)_3]_3$ and those which contain triphenylphosphane or alkyl or aryl ammonium salts of sulfonated or carboxylated triarylphosphanes of the general formula:

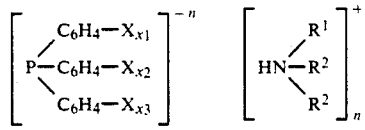

as ligands. In the above general formula, X is a sulfonate ($SO_3$) or carboxylate radical (COO); $x^1$, $x^2$, and $x^3$ are 0 or 1; $R^1$ and $R^2$ are the same or different alkyl radicals having 4 to 12 carbon atoms or aryl or cycloalkyl radicals having 6 to 12 carbon atoms, and $R^1$ also denotes hydrogen. These compounds and their use are explained in slightly more detail hereafter. Naturally, it is not intended to restrict the scope of the invention to the separation of this special compound class.

In such catalyst systems, disulfonated and trisulfonated, or dicarboxylated and tricarboxylated triphenylphosphanes, are particularly suitable as ligand anions. The compounds do not need to be used in pure form, but can also be used as a mixture or disubstituted and trisubstituted phosphanes.

The cations of the ligands are derived from secondary or tertiary amines. Preference is given to amines containing a total of 16 to 36 carbon atoms. Examples are di-2-ethylhexylamine, diisooctylamine, diisononylamine, tri-n-octylamine, triisooctylamine, triisononylamine, triisodecylamine.

Apart from the phosphanes, the rhodium complex compounds can contain other ligands such as H, CO, amines, and π-aromatics, e.g. cyclopentadienyl or π-olefins such as 1,5-cyclooctadiene.

Together with the phosphane ligand present in excess, the rhodium compounds form a catalyst system which, when homogeneously dissolved in the organic reaction medium, can, for example, be used in the hydroformylation of olefinically unsaturated compounds. The term olefinically unsaturated compounds includes straight and branched chain olefins, regardless of the position of the double bond in the molecule, as well as cycloolefins such as n-hexene-1, n-heptene-1, n-octene-1, n-nonene-1, diisobutylene, tripropylene, cyclohexene, and cyclooctene. The olefinically unsaturated compounds also include dienes such as 1,3-butadiene, 1,5-hexadiene, and dicyclopentadiene, as well as compounds containing functional groups such as acrylic acid, acrylic acid ester, acrylonitrile, methacrylic acid, methacrylic acid ester, vinyl ester, vinyl ether, and acrolein.

The reaction mixture formed during the hydroformylation of the olefinic compound contains, for example, mainly the reaction product, an aldehyde, by-products such as the alcohol derived from the aldehyde, as well as higher-boiling addition and condensation products of the aldehyde. Furthermore, a solvent serving as the reaction medium can also be present.

Before the organic components of the reaction mixture are isolated, e.g. by distillation, the rhodium complex compound is generally separated. It is normally present in the mixture in a concentration of 1 to 1,000, in particular, 3 to 400 and preferably 20 to 200 ppm. According to the new procedure it is now possible to almost completely separate the rhodium compound from the reaction product. In this connection it is particularly important that the rhodium compound is recovered in a form which permits its immediate re-use in the synthesis.

The following describes the preparation of a type of membrane which can be used in the process according to the invention. There is also a description of the separation of organometallic compounds or metal carbonyls from reaction mixtures with the membrane using the new procedure.

Preparation of the membrane

The polyaramide is prepared by condensation of
97-99 mole % terephthalic acid dichloride
25 mole % p-phenylene diamine
25 mole % 1,4-bis(4-aminophenoxy)benzene
50 mole % 3,3'-dimethylbenzidine
in N-methylpyrrolidone as a solvent. Enough terephthalic acid dichloride is used so that the polyaramide has a Staudinger index of 200 to 300 ml/g. The amount of solvent is dosed so that a solution is formed containing about 7% by weight polycondensate. After condensation has taken place, the hydrogen chloride loosely bound to the solvent is neutralized by the addition of 100 mole % CaO. Then 5% by weight anhydrous calcium chloride (based on the polymer solution) is dissolved with stirring in the reaction mixture. The solution is gently warmed, filtered, and degassed. It can be used directly for the preparation of the membrane.

It is possible to prepare the membrane either without a support or on a polyester non-woven fabric as a support. In the following, the preparation of a support-free membrane is described. The slightly warmed polyaramide solution is spread onto a glass plate with a doctor blade to form a uniform film with a thickness of about 150μ and then immersed in a water bath at a temperature of 2° C. After approximately 20 minutes the membrane is pulled off the glass plate and placed in hot water at a temperature of 100° C. for 5 minutes. Then the membrane is placed in i-propanol to replace the pore liquid (water) with alcohol. The membrane is then placed in toluene for approximately 10 hours; after this treatment it is suitable for performing separations. During all these operations, care must be taken to insure that the membrane does not dry out.

EXAMPLE 1

The separation of the catalyst, which consists of a rhodium complex compound and the triisooctylammonium salt of tris(m-sulfophenyl)phosphane, from the raw product of the hydroformylation of dicyclopentadiene (DCP) is described below.

The separation is performed with 2,646 g of raw product which contains TCD-monoaldehyde and TCD-dialdehyde (TCD=tricyclodecane) in a weight ratio of 18:98.2; 24.8 ppm of rhodium (corresponding to 65.6 mg); a total of 698 ppm of phosphorus, i.e. P(III) and P(V) (corresponding to 1,846.9 mg) of which there are 17.4 mmoles of P(III)/kg (corresponding to 1,427.2 mg); as well as toluene as a solvent.

The raw product is passed at 40° C. and a pressure of 0.5 MPa into a metal cell which is fitted with a membrane having a surface area of 20 cm² manufactured as described. Any solution which does not diffuse through the membrane is circulated at a rate of approximately 8 l/h. The pass-over rate is approximately 0.15 m/sec.

After the experiment has been completed, 2,139.4 g of permeate (81% of the feed) and 486.6 g of retentate (18.4% of the feed) are obtained. The permeate contains a total of 357.3 mg of phosphorus (19.3% of the feed), of which 172.4 mg is a P(III) compound (12.1% of the feed), and 2.29 mg of rhodium (3.5% of the feed). The retentate contains a total of 77.9% phosphorus (based on the feed) and 95% of the rhodium (based on the feed). The permeate flow is 12 l/(m²×h) at the beginning of separation and 5 l/(m²×h) at the end.

Under the temperature and pressure conditions of the first separating stage, 1,933 g of the permeate are subjected to a second membrane filtration. The permeate flow is 17.5 l/(m²×h) at the beginning of the experiment and 10 l(m²×h) at the end. The results of the separation are compiled in Table 1.

TABLE 1

|  |  | Permeate | Retentate |
|---|---|---|---|
| amount | (% of feed) | 73.1 | 7.2 |
| P III | (% of feed) | 8.8 | 13.1 |
| Total P | (% of feed) | 5.6 | 13.2 |
| Rh | (% of feed) | 0.4 | 4.3 |

Example 1 shows that, when the claimed process is used, over 99.5% of the rhodium and 94.4% of the phosphorus (III) compound are retained.

EXAMPLE 2

The combined retentates from Example 1 are used as a catalyst for the hydroformylation of DCP in toluene as a solvent. After the reaction has been completed, GC analysis shows a conversion of 97.8% and a ratio of monoaldehyde to dialdehyde of 2.0:98.0. At 40° C. and a pressure of 0.5 MPa the permeate flow is 10.5 l/(m²×h) at the beginning and 3.6 l(m²×h) at the end of separation. The retention rates correspond to those of Example 1.

Example 2 shows that, according to the claimed process, the catalyst system and the excess ligand can be separated and recirculated in their active forms.

EXAMPLE 3

Solutions containing higher concentrations of metal complex compounds can also be successfully treated according to the new procedure. The product of the hydroformylation of DCP using the catalyst system of Example 1 but with an Rh concentration of 102 ppm is used as a starting material. It contains TCD-dialdehyde, 16.5 mmoles of P(III)/kg, a total of 681 ppm of phosphorus and, in addition, toluene as a solvent.

Separation takes place under the temperature and pressure conditions and using the cell of Example 1. In the first run, the permeate flow is 10 l/(m²×h) at the beginning of the experiment and 3 l/(m²×h) at the end; in the second run, in which the permeate of the first separation is used, 17 and 9 l/(m²×h).

The results of the separation are compiled in Table 2.

TABLE 2

|  |  | Permeate I/II | | Retentate I/II | |
|---|---|---|---|---|---|
| amount | (% of feed) | 2,383.0 | 2,119 | 403.8 | 217 |
| P III | (% of feed) | 12.9 | 8.7 | 67.0 | 12.3 |
| Total P | (% of feed) | 16.8 | 6.3 | 76.5 | 12.0 |
| Rh | (% of feed) | 2.5 | 0.2 | 96.3 | 2.9 |

Example 3 shows that the amount of metal and ligand retained is not reduced even at higher rhodium concentrations.

EXAMPLE 4

420 g of a product from the hydroformylation of hexadiene-1,5 with rhodium and triphenylphosphane as catalysts are separated according to the claimed process using the membrane cell of Example 1. The Oxo raw product contains 333 ppm of Rh and 30% toluene. The ratio of monoaldehyde to dialdehyde is 15 to 85. The permeate flow at 40° C. is 5 l/(m²×h).

The membrane filtration leads to the results compiled in Table 3.

TABLE 3

|  | Permeate | Retentate |
|---|---|---|
| Amount (g) | 137 (32.4% of feed) | 270 (67.5% of feed) |
| Rh (ppm) | 192 (19% of feed) | 400 (81% of feed) |

As can be seen, 80% of the rhodium contained in the raw product is separated.

The following examples demonstrate the advantageous physical properties of the membrane used in accordance with the present invention. A membrane with an average thickness of 270μ manufactured and located in a cell according to the aforementioned regulations is used.

For separation, the reaction mixture of the hydroformylation of DCP with rhodium and the triisooctylammonium salt of tris(m-sulfophenyl)phosphane as catalysts is used. The rhodium concentration in the Oxo raw product is 25.4 ppm, it also contains 23.4 mmoles in total of phosphorus/kg, 0.013 moles of P(III) and approximately 55% toluene. The ratio of monoaldehyde to dialdehyde is 2:98. The amount of rhodium and phosphorus retained in Examples 5 to 10 is roughly the same as in Example 1.

EXAMPLE 5

For conditioning, the membrane is first measured for thickness, washed with acetone and then with isopropanol, and then installed into the apparatus while it is still moist from the isopropanol. Immediately afterwards, the apparatus is filled with toluene and the isopropanol is displaced from the membrane by washing it out.

Then the permeate flow is measured at 25° C. and 0.3 MPa. It stabilizes very quickly from 22 $1/(m^2 \times h)$ at the beginning to 18 to 19 $1/(m^2 \times h)$.

EXAMPLE 6

In order to determine the permeate flow and the properties of the membrane compared with a rhodium and phosphane-free, raw TCD-dialdehyde from the hydroformylation of DCP, the toluene is displaced by a product freed from rhodium and phosphane by another means. The permeate flow of the membrane does not change.

This experiment shows that the membrane remains stable in the Oxo raw product, i.e. no swelling takes place.

EXAMPLE 7

At 0.3 MPa and 25° C. the membrane is fed with the Oxo raw product described above. Over a period of one hour, the permeate flow is determined in 12 measurements. Immediately, an average constant permeate flow of 5.7 $1/(m^2 \times h)$ establishes itself.

EXAMPLE 8

At a pressure of 0.5 MPa, but otherwise under the same conditions as in Example 7, the permeate flow is determined in 6 individual measurements over a period of 30 minutes. An average value of 9.7 $1/(m^2 \times h)$ is determined. Example 8 shows an almost linear rise in the permeate flow with a pressure differential of 0.3 to 0.5 MPa.

EXAMPLE 9

By gradually increasing the temperature from 25° C. to 40° C., the permeate flow rises continuously to 13.6 $1/(m^2 \times h)$. Thus, its temperature coefficient is about +2.5%/°C.

EXAMPLE 10

The raw product from the hydroformylation of DCP used in the previous examples is again replaced by toluene. The permeate flow rises spontaneously to 40 $1/(m^2 \times h)$ at 41° C. and stabilizes at 26 $1/(m^2 \times h)$ at 27° C. and 0.5 MPa. After 1 hour the experiment is interrupted, the membrane removed and its thickness measured. There is almost no change in the thickness. Example 10 shows that the membrane does not clog or foul and that it remains stable. Examples 5 to 10 all prove the efficiency of the new process.

EXAMPLE 11

The previously used membrane cell with a polyaramide membrane prepared according to the manufacturing process described above receives a $C_9$ aldehyde from the high-pressure hydroformylation of diisobutylene with rhodium. The rhodium content in the Oxo raw product (the metal being present as a carbonyl compound) is 4.3 ppm. The product contains no phosphorus. The permeate flow is 39 $1/(m^2 \times h)$ at the beginning of the experiment at 40° C. and 0.5 MPa. It falls to 16.8 $1/(m^2 \times h)$ when there is a transition to the $C_9$ Oxo raw product in the first run and is 11.6 $1/(m^2 \times h)$ at the end of the experiment; the permeate flows in the second run (feed of the permeate of the first separation) are 14.5 and 10.1 $1/(m^2 \times h)$.

The results are compiled in Table 4.

TABLE 4

|  | Permeate 1 | Permeate 2 | Retentate 1 | Retentate 2 |
|---|---|---|---|---|
| Amount (g) | 625 | 517 | 132 | 104 |
| Rh (% of feed) | 52 | 18 | 35 | 27.9 |

After the experiment has been completed and the Oxo raw product replaced by toluene, a permeate flow of 40 $1/(m^2 \times h)$ is again obtained.

What we claim is:

1. A process for concentrating solutions of organometallic compounds and/or metal carbonyls in an organic media by ultrafiltration or dialysis, said process comprising contacting said solutions with a semi-permeable polyaramide membrane having a retention side and a permeation side opposite said retention side, said membrane being permeable only to said organic media.

2. The process of claim 1 wherein there is a pressure difference between said retention side and said permeation side.

3. The process of claim 2 wherein said pressure difference is greater than an osmotic pressure of said system.

4. The process of claim 2 wherein said difference is 0.2 to 2.0 MPa.

5. The process of claim 1 wherein there is a difference in concentration between said retention side and said permeation side and said separation is carried out by dialysis.

6. The process of claim 5 wherein a flushing solution flows in contact with said permeation side.

7. The process of claim 6 wherein said flushing solution flows countercurrently to said feed.

8. The process of claim 6 wherein said flushing liquid is an organic solvent.

9. The process of claim 6 wherein said flushing solution flows concurrently with said feed.

10. The process of claim 1 wherein said organometallic compound has a carbon atom linked to a first metal directly or through a nitrogen, oxygen, or sulfur atom.

11. The process of claim 10 wherein said first metal is selected from the group consisting of boron, silicon, phosphorous, and Groups IVA, VA, VIA, VIIA, VIIIA, and IB of the Periodic Table.

12. The process of claim 11 wherein said first metal is selected from the group consisting of manganese, cobalt, nickel, palladium, platinum, iridium, and rhodium.

13. The process of claim 1 wherein said organic metallic compound is selected from the group consisting of acetyl acetonate and dimethylglyoximes.

14. The process of claim 1 wherein said metal carbonyl contains at least one additional ligand.

15. The process of claim 14 wherein said additional ligands are selected from the group consisting of hydrogen, olefins, phosphanes, acetates, and benzonitriles.

16. The process of claim 1 wherein said metal carbonyl has a second metal and a carbonyl group, said second metal being linked directly to said carbonyl group.

17. The process of claim 16 wherein said second metal is selected from the group consisting of Groups VIA, VIIA, and VIIIA of the Periodic Table.

18. The process of claim 11 wherein said second metal is selected from the group consisting of iron, cobalt, nickel, ruthenium, rhodium, and iridium.

19. The process of claim 1 wherein said membrane is the product of a polycondensation reaction of an aromatic dicarboxylic acid or derivative thereof with an aromatic diamine.

20. The process of claim 19 wherein said polycondensation reaction is in the presence of a dipolar, aprotic solvent.

21. The process of claim 20 wherein said solvent is N-methyl-2-pyrollidone.

22. The process of claim 19 wherein said aromatic dicarboxylic acid or derivative is selected from the group consisting of terephthalic acid, 4,4'-diphenyldicarboxylic acid, 4,4'-diphenyletherdicarboxylic acid, 4,4'-diphenylsulfonedicarboxylic acid, and 2,6-naphthalene dicarboxylic acid.

23. The process of claim 19 wherein said aromatic diamine is selected from the group consisting of p-phenyldiamine, 3,3'-dimethoxybenzidine, 3,3'-dichlorobenzidine, 3,3'-dimethylbenzidine, 4,4'-diaminodiphenylmethane, 2,2-bis(4-aminomethyl) propane, and 1,4-bis(4-aminophenoxy)benzene.

24. The process of claim 19 wherein said membrane is precipitated by adding water after said polycondensation reaction, immersing said membrane isopropanol at least once, and then immersing said membrane in said organic medium.

25. The process of claim 1 wherein said polyaramide membrane is the reaction product of terephthalic acid with p-phenylene diamine, 1,4-bis(4-aminophenoxy) benzene, and/or 3,3'-dimethylbenzidene.

26. The process of claim 1 wherein said polyaramide membrane has a molecular weight of 5,000 to 200,000.

27. The process of claim 26 wherein said molecular weight is 10,000 to 50,000.

28. The process of claim 1 wherein said membrane is integrally asymmetric.

29. The process of claim 1 wherein said membrane comprises a porous support and an active layer.

30. The process of claim 29 wherein said active layer has a thickness of $0.05\mu$ to $5.0\mu$.

31. The process of claim 29 wherein said membrane has a thickness of 10 to $400\mu$.

32. The process of claim 31 wherein said membrane has a thickness of 50 to $200\mu$.

33. The process of claim 1 wherein said membrane comprises hollow-fibers and/or capillaries.

34. The process of claim 1 wherein said membrane is preheated by immersing it in said organic medium.

35. The process of claim 1 which is carried out at a process temperature of 0° to 200° C.

36. The process of claim 35 wherein said process temperature is 40° to 130° C.

37. The process of claim 1 wherein said metal compound comprises not more than 20% by weight of said organic medium.

38. The process of claim 37 wherein said metal compound is 2 to 400 ppm by weight based on said organic medium.

39. The process of claim 1 wherein said feed is at a flow velocity of 0.1 to 10 meters/second.

40. The process of claim 39 wherein said flow velocity is 0.5 to 2.5 meters/second.

41. The process of claim 1 wherein said metal compound has a particle size of at least 50% larger than any other organic compound present.

42. The process of claim 1 wherein said separation is carried out in a plurality of stages.

43. The process of claim 42 wherein said stages are in parallel.

44. The process of claim 42 wherein said stages are in series.

45. The process of claim 1 wherein said metal compound is selected from the group consisting of nickel/aluminum complexes, cobalt/aluminum complexes, phosphate-modified nickel/aluminum alkyl compounds, $Pd(CH_3COO)_2/P(CH_2H_5)_3$ complexes, $RuHCl[P(C_6H_5)_3]_3$, $RhCl[P(C_6H_5)_3]_3$, $RhCO[P(C_6H_5)_3]_2$, $Ni[P(p-C_6H_4CH_3)_3]_4/H^+$, $Ir(COD)[P(C_6H_{11})_3]Py$ (COD=1,5-cyclooctane, Py=pyridine), $RuCl_2[P(C_6H_5)_3]$, $Ru(BINAP)(ClO_4)_2$ (BINAP=2,2' bis(diphenylphosphino) 1,1'-binaphthyl), $HRhCO[P(C_6H_5)_3]_3$, $Pd[P(C_6H_5)_3]_4$, and complexes containing compounds of the formula

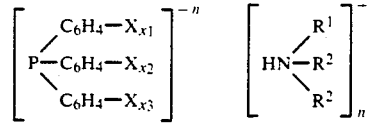

wherein X is a sulfonate ($SO_3$) or carboxylate radical (COO); $x^1$, $x^2$, and $x^3$ are 0 or 1; $R^1$ and $R^2$ are the same or different alkyl radicals having 4 to 12 carbon atoms or aryl or cycloalkyl radicals having 6 to 12 carbon atoms, and $R^1$ also denotes hydrogen.

46. The process of claim 1 wherein said metal compound is of rhodium and said compound is present in a catalyst amount of 1 to 1000 ppm based on said organic medium.

47. The process of claim 46 wherein said catalyst amount is 3 to 400 ppm.

48. The process of claim 47 wherein said catalyst amount is 20 to 200 ppm.

49. A process for concentrating solutions of non-dissociable organometallic complexes and/or metal carbonyl complexes and excess ligands in an organic media by ultrafiltration or dialysis, said process comprising contacting said solutions with a semi-permeable polyaramide membrane having a retention side and a permeation side opposite said retention side, said membrane being permeable only to said organic media.

* * * * *